US005470546A

United States Patent [19]
Hall

[11] Patent Number: 5,470,546
[45] Date of Patent: Nov. 28, 1995

[54] APPARATUS FOR STORING AND STERILIZING BIO-HAZARDOUS WASTE

[76] Inventor: John L. Hall, 8444 Julie Lynne Cir., Tracy, Calif. 95376

[21] Appl. No.: 264,988

[22] Filed: Jun. 24, 1994

[51] Int. Cl.⁶ .................................................. A61L 2/06
[52] U.S. Cl. .................... 422/292; 422/297; 422/299; 422/300; 422/307; 588/258; 588/900
[58] Field of Search ........................ 422/292, 297, 422/299, 300, 307, 308, 905, 26; 588/258, 900; 100/73

[56] References Cited

U.S. PATENT DOCUMENTS

| | | | |
|---|---|---|---|
| 3,351,422 | 11/1967 | Jones et al. | 422/299 |
| 3,980,431 | 9/1976 | Anderson | 422/297 X |
| 3,994,684 | 11/1976 | Tomasulo | 422/297 |
| 4,374,491 | 2/1983 | Stortroen et al. | 100/73 |
| 4,670,227 | 6/1987 | Smith | 422/297 |
| 5,084,250 | 1/1992 | Hall | 422/292 |
| 5,213,775 | 5/1993 | Ghiretti | 422/297 X |
| 5,348,704 | 9/1994 | Tanaka | 422/300 X |

*Primary Examiner*—Robert J. Warden
*Assistant Examiner*—Krisanne M. Thornton
*Attorney, Agent, or Firm*—Harris Zimmerman

[57] ABSTRACT

A fluid tight waste materials receptacle is located within a housing which has an upper access opening through which infectious wastes from medical clinics or the like may be deposited in the receptacle. A lower access opening enables entry and withdrawal of a sterilized waste receiver which may, for example, be a wheeled cart. The receptacle has an open end and a closed end and is pivotable between a first orientation at which the open end is coincident with the upper access opening in order to receive wastes and a second orientation at which the open end is turned downward to discharge wastes into the receiver. A closure pivoted to the housing seats in and seals the open end of the receptacle when it is at the first orientation. The receptacle is periodically evacuated and steam is admitted to sterilize the contents prior to discharge into the receiver.

14 Claims, 3 Drawing Sheets

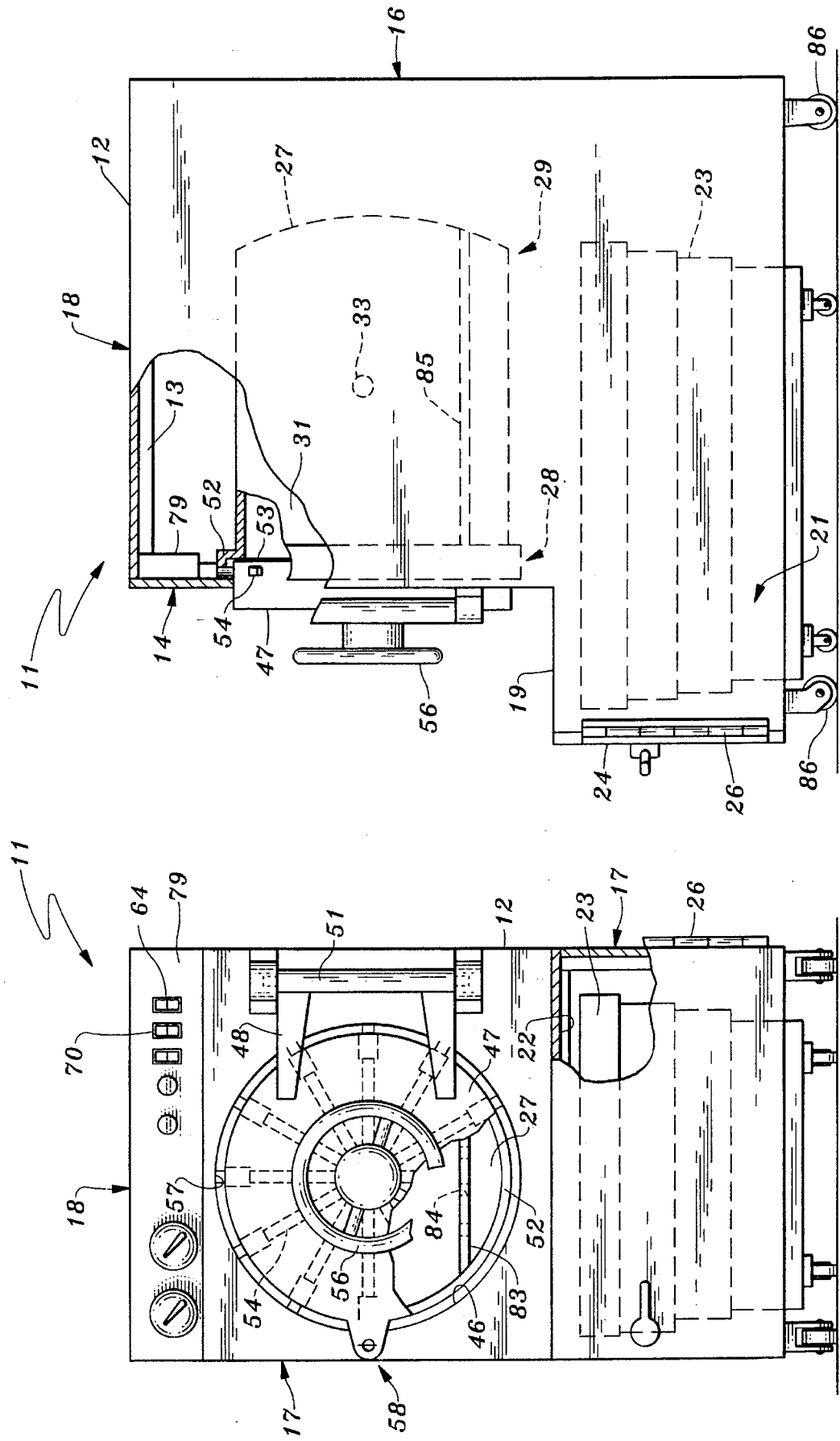

5,470,546

APPARATUS FOR STORING AND STERILIZING BIO-HAZARDOUS WASTE

TECHNICAL FIELD

This invention relates to apparatus for processing bio-hazardous or infectious waste materials and more particularly to apparatus of this kind in which accumulations of such wastes are sterilized prior to disposal of the material at a landfill or the like.

BACKGROUND OF THE INVENTION

Hospitals, medical clinics and the like generate waste materials which require special processing prior to disposal of the material. Used bandages, hypodermic needles, specimen containers and tissues, for example, may be contaminated with infectious viruses or bacteria. Wastes of this kind must be stored in closed containers and be rendered harmless prior to disposal at a garbage dump or the like.

Processing of such wastes by incineration is subject to a number of problems. Much of the waste may have a high moisture content and be composed of materials which are not readily combustible. Consequently, fuel requirements are high and the incinerators are costly to operate. Equipment costs and operating costs are further aggravated by the need to suppress release of pollutants into the surrounding environment.

Prior U.S. Pat. Nos. 4,374,491 and 5,084,250 disclose a more economical alternative type of infectious waste processor. The apparatus of these prior patents sterilizes the waste by exposure of the wastes to high pressure steam. Fuel costs are relatively low and prevention of pollutant release can be more easily accomplished.

The waste processors described in the above identified prior patents also function as a temporary storage for non-hazardous wastes and include mechanism for compacting the wastes prior to transport of the material to a dump site. These additional functions make the apparatus particularly suitable for use at hospitals or the like which generate large amounts of infectious wastes.

The compaction mechanism significantly increases the bulk and cost of the apparatus both directly and indirectly as structural complications are needed to enable transfer of wastes from the sterilizer to the compactor. Small medical clinics which produce relatively small amounts of waste may not need the benefits of these complications and may find the cost of the apparatus to be a difficult financial burden. Thus there is a need for a simplified and more compact waste sterilizer.

The present invention is directed to overcoming one or more of the problems discussed above.

SUMMARY OF THE INVENTION

In one aspect, the present invention provides apparatus for sterilizing bio-hazardous waste materials which includes a housing having a front face with an upper access opening for enabling entry of waste materials. A lower access opening enables entry and withdrawal of a removable sterilized waste receiver. An unsterilized waste receptacle in the upper region of the housing has an open end and a closed end and is pivotable about a horizontal pivot axis which extends in parallel relationship with the front face of the housing. The receptacle is pivotable between a first orientation at which the open end is in register with the upper access opening of the housing and an upended orientation at which the open end is below the closed end and at least partially faces the lower region of the housing. A closure is coupled to the housing and means are provided for enabling movement of the closure between an open position at which unsterilized waste materials may be inserted into the receptacle through the upper access opening when the receptacle is at its first orientation and a closed position at which the closure seats at and closes the open end of the receptacle. The apparatus further includes means for sterilizing waste materials within the closed receptacle.

In another aspect of the invention, apparatus for storing and sterilizing bio-hazardous wastes includes a housing having a front wall, back wall and opposite side members. An upper access opening in the front wall enables insertion of wastes which are to be sterilized and a lower access opening is proportioned to enable insertion of a sterilized waste receiver and withdrawal of the receiver. A fluid tight unsterilized waste receiver in the housing has an open end and a closed end. Pivot means enable pivoting of the receptacle between a first orientation at which the open end is substantially coincident with the upper access opening and a second orientation at which the open end faces at least partially in a downward direction. The receptacle pivots about an axis of rotation that is parallel with the front wall of the housing and the upper access opening. A receptacle closure at the front wall of the housing is pivoted to the housing and is movable between an open position at which the open end of the receptacle is exposed at the upper access opening of the housing and a closed position at which the closure seats at the open end and seals the receptacle. The apparatus further includes means for sterilizing waste material within the receptacle when it is at the first orientation and is being sealed by the closure.

The invention provides a more economical installation for processing bio-hazardous wastes at medical facilities or the like. Wastes of this kind are typically deposited in plastic bags which are initially used as liners for waste baskets or the like. The unsterilized waste receptacle of the apparatus may be used as a sealed temporary storage for the bagged wastes. Periodically the accumulated wastes may be sterilized, without further handling, by activating the sterilizing means which may, for example, evacuate air from the receptacle and then inject pressurized steam. The sterilized wastes may then be dumped into an underlying cart or other receiver without manual handling by activating the pivot means which turns the receptacle about a transverse axis. The apparatus may be relatively compact in comparison with prior waste sterilizers of the general type.

The invention, together with further aspects and advantages thereof, may be further understood by reference to the following description of the preferred embodiment and by reference to the accompanying drawings.

BRIEF DESCRIPTION OF THE DRAWINGS

FIG. 1 is a broken out front elevation view of a bio-hazardous waste processor in accordance with the preferred embodiment of the invention.

FIG. 2 is a broken out side elevation view of the waste processor of FIG. 1.

DETAILED DESCRIPTION OF THE PREFERRED EMBODIMENT

Figure 3:
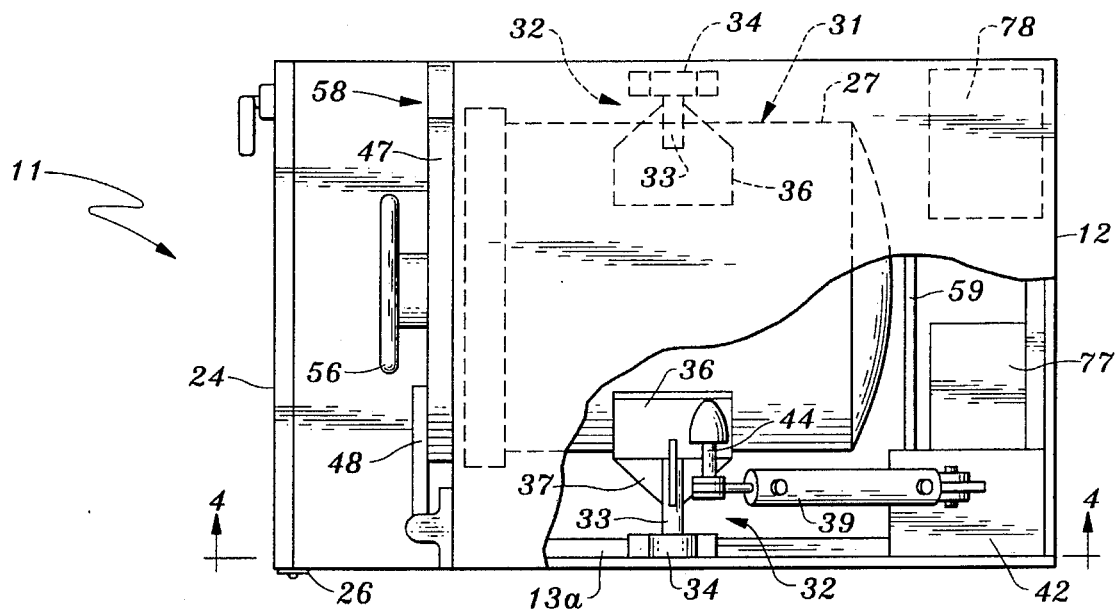
FIG. 3 is a broken out top view of the apparatus of the preceding figures.

Referring initially to FIGS. 1 and 2 of the drawings in conjunction, a bio-hazardous waste processor 11 in accordance with this example of the invention has a housing 12 which includes frame members 13 that support a front wall 14, rear wall 16, opposite side walls 17 and a top wall 18. The housing 12 of this embodiment has an open underside.

Front wall 14 is of less length in the vertical direction than the side walls 17 and is situated at the upper region of the housing. A horizontal shelf 19 extends outward from the lower edge of front wall 14 and the portions 21 of side walls 17 which are below the front wall extend outward for a similar distance. The forward edges of shelf 19 and the forward edges of side wall portions 21 jointly define a lower access opening 22 at the front of housing 12. The opening 22 is proportioned to enable entry and withdrawal of a sterilized waste receiver 23 which is preferably a wheeled cart. Opening 22 may be provided with a latchable door 24, fastened to one of the side walls 17 by a hinge 26, although this is not essential in all cases as the contents of receiver 23 have been sterilized and rendered non-infectious.

Figure 4:
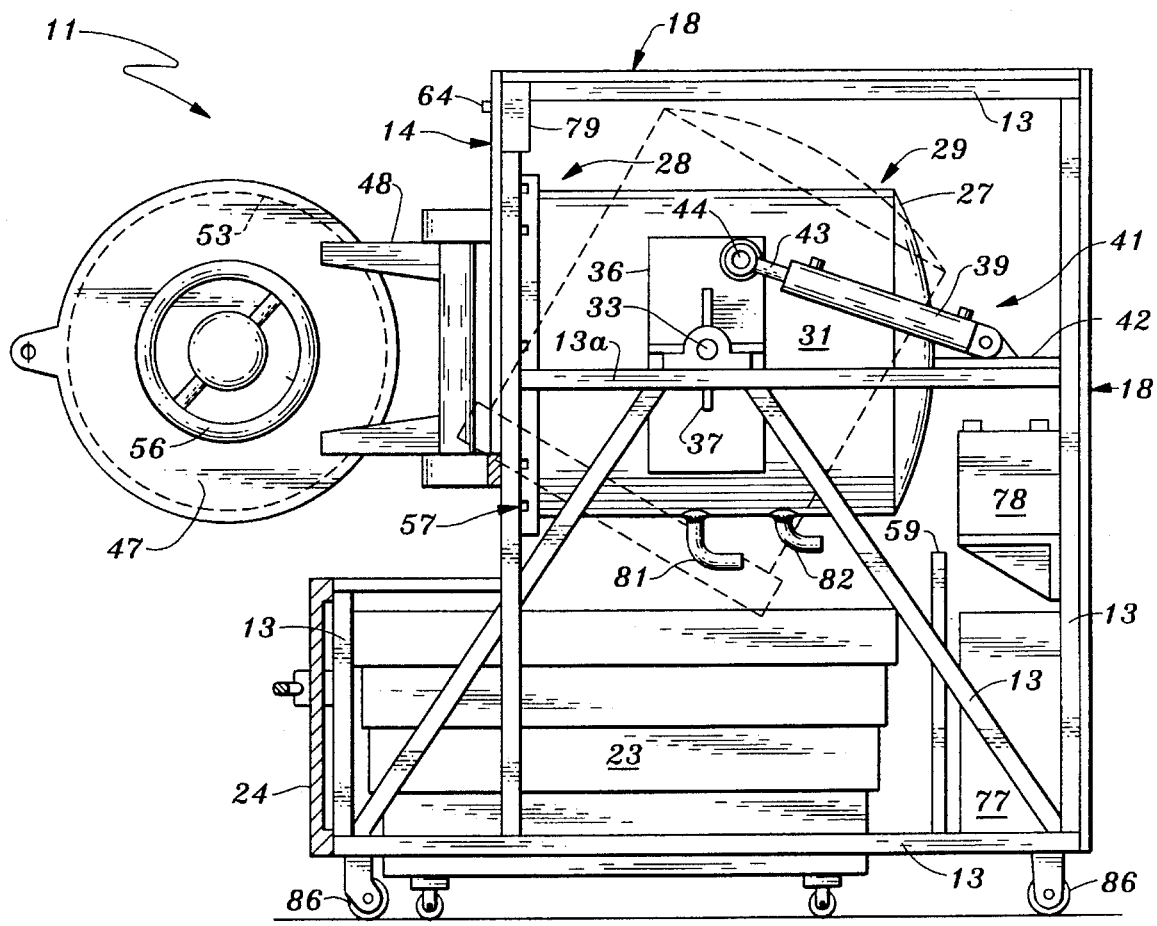
FIG. 4 is a section view of the waste processor taken along line 4—4 of FIG. 3 except insofar as a waste receptacle closure is shown in the closed position in FIG. 3 and in the open position in FIG. 4.

Wastes which are to be sterilized are deposited in a fluid tight receptacle 27 which is within the upper region of housing 12. The receptacle 27 has an open front end 28 and a closed back end 29 and a cylindrical side wall 31 in this example although the receptacle may have other configurations. Referring now to FIGS. 3 and 4, the receptacle 27 may be pivoted between a first orientation at which the open end extends vertically and is adjacent to the inside surface of housing front wall 14 and an upended position at which the open end 28 is below the closed end 29 and faces at least partially in a downward direction in order to dump the contents of the receptacle into receiver 23. For this purpose, the receptacle 27 is supported by pivot couplings 32 formed by a pair of aligned axles 33 which extend outward from opposite sides of the receptacle 27 to bearings 34 which are secured to horizontally extending frame members 13a at opposite sides of the housing 12. Curved plates 36 are welded to the side wall 31 of receptacle 27 to reinforce the side wall and triangular gussets 37 extend between plates 36 and the axles 33 to further strengthen the construction.

Pivot couplings 32 are located to provide an axis of rotation which intersects the receptacle 27 at a location which is between the ends 28 and 29 and between the portions of the receptacle side wall 31 that are uppermost and lowermost when the receptacle is at the first or horizontal orientation. Preferably, the pivot couplings 32 are at a substantially centered location on the receptacle side wall 31. This minimizes the amount of clearance space that must be provided within housing 12 to accommodate to the pivoting of the receptacle and also enables pivoting of the receptacle with a minimal amount of force.

Linkage can be provided to enable manual pivoting of receptacle 27 between the two orientations of the receptacle but it is preferable to motorize the operation. In this example a hydraulic ram 39 is used for the purpose. The head end 41 of the ram is pivoted to a bracket 42 which is behind the receptacle and which is secured to housing frame member 13a. The extensible and retractable rod 43 of the ram 39 extends forward and upward along the side wall 31 of the receptacle 27 and is pivotably coupled to a pin 44 which extends outward from the side wall at a location that is higher than the axis of rotation about which the receptacle pivots. Ram 39 positions receptacle 27 at its first or horizontal orientation when the ram is fully contracted and at its second or waste dumping orientation when the ram is fully extended.

The hydraulic ram 24 of this embodiment of the invention may be replaced with other means for pivoting receptacle 27, such as an electrically powered actuator for example.

Referring jointly to FIGS. 1 and 4, access to waste receptacle 27 is provided for by an upper access opening 46 situated in the front wall 14 of housing 11. Opening 46 has a configuration, circular in this example, that conforms with the configuration of the open end 28 of receptacle 27 and is of similar size. Thus the opening 46 and the open end 28 of receptacle 27 are substantially coextensive when the receptacle is at its first or horizontal orientation.

A closure 47 seats in the open end 28 of receptacle 27 except at times when infectious material is being deposited in the receptacle or when sterilized wastes are being dumped into receiver 23. Closure 47 is hinged to housing 13 by arms 48 which extend from a rotatable vertical post 51 at one side of the upper access opening 46. The closure 47 has a circular configuration conform-to the open end 28 of receptacle 27 and seats in an annular stepped flange 52 which forms the open end of the receptacle. An annular seal 53 is carried by the closure 47 and is compressed against flange 52 to provide a hermetic or fluid tight sealing of the receptacle. The closure 47 may be of any of the known types that are used to provide a pressure resistant sealing effect. In this example the closure 47 is a door of the form which has radially directed latching arms 54 which can be translated and pivoted by turning of an actuator wheel 56 to enter the arms into openings 57 in flange 52 and to cause the closure to exert pressure against seal 53. The detailed construction of doors of this kind, which are extensively used to seal openings in the bulkheads of ships, is known to the art.

Closure 47 may be provided with a lock 58 of the key or combination type to prevent unauthorized opening of the infectious waste receptacle 27.

Referring again to FIGS. 3 and 4, a transverse partition 59 extends between housing side walls 17 within the lower region of the housing at a location which assures that the sterilized waste receiver 23 is positioned correctly to receive material which is dumped from receptacle 27.

Waste sterilization is effected by heating the contents of receptacle 27. This is preferably accomplished by evacuating air from the sealed receptacle 27 and then injecting pressurized steam. Evacuation of air removes air from the plastic bags in which the wastes are typically contained. This shortens processing time as such air can otherwise act as a thermal insulator which slows heat transfer to the contents of the bags.

Figure 5:
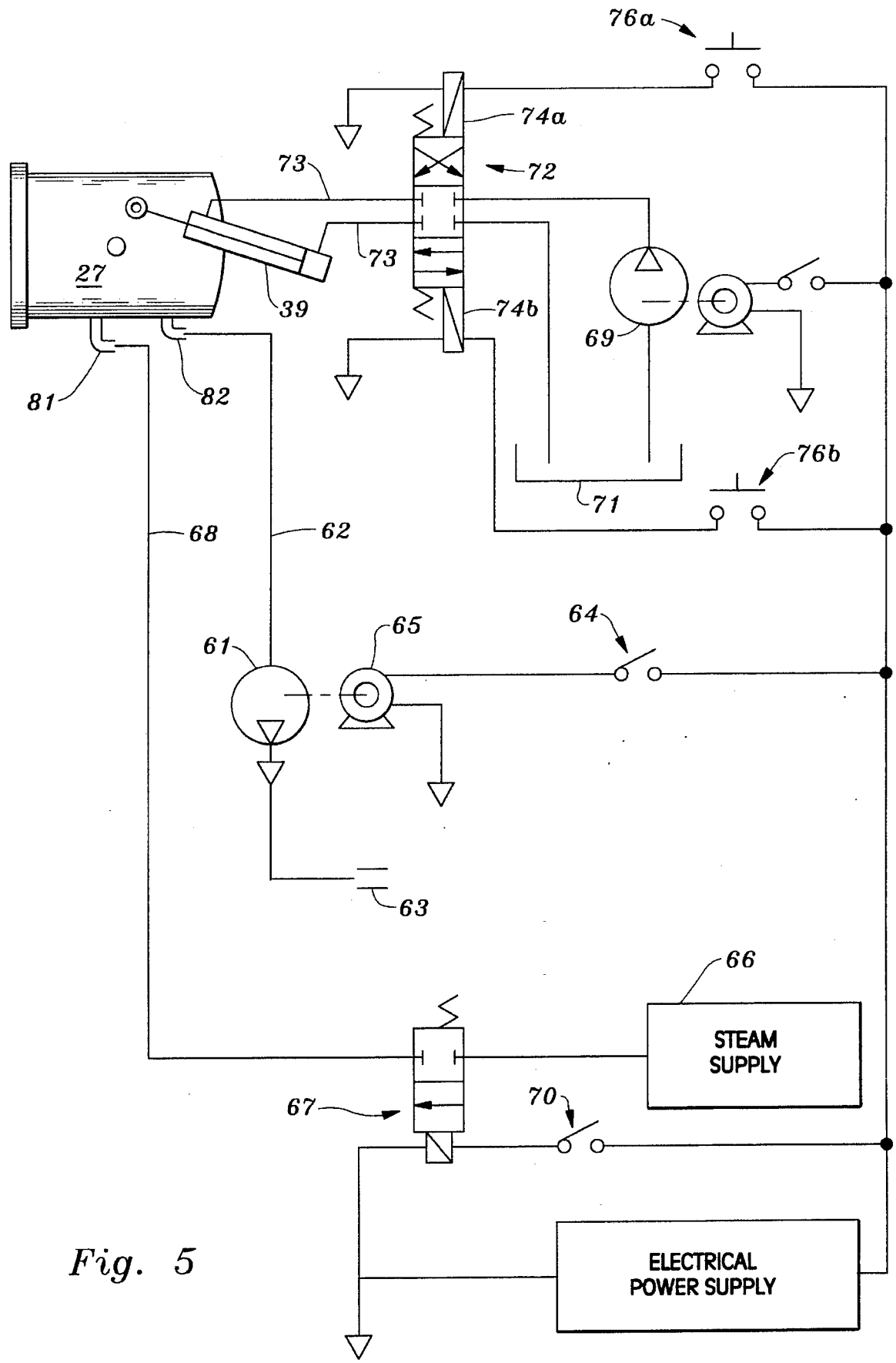
FIG. 5 is a schematic fluid circuit diagram depicting the steam injection system, vacuum pumping system and a hydraulic ram and control valve which are components of the apparatus of the preceding figures.

Referring now to FIG. 5, fluid circuit components for effecting the sterilization include a vacuum pump 61 having an inlet which is communicated with the interior of receptacle 27 through a flexible hose 62 and an outlet connected to a vent 63. Vacuum pump 61 in this example is driven by an electrical motor 65 which is actuated and deactuated by a manually operated switch 64 but such components can take other forms. The pump 61 may for example be of the aspirator type which is operated by a flow of steam. Cycling of controls such as switch 64 may be automated and be under the control of a microprocessor. Steam from a steam source 66 is transmitted to the interior of receptacle 27 through a solenoid piloted flow control valve 67 and another flexible hose 68 in response to closing of another switch 70. Hospitals and the like often have a pre-existing source of piped steam to which the flow control valve 67 may be connected. If a preexisting supply is not available, a steam generator may be installed at a location near the waste processor 11 or internally within the waste processor.

A motor driven pump 69 draws hydraulic fluid from a reservoir 71 and provides pressurized fluid for operating the hydraulic ram 39. A ram control valve 72 receives the fluid from pump 69 and is communicated with the ram 39 through a pair of flexible hoses 73 one of which communicates with the head end of the ram and the other of which communicates with the rod end of the ram. The control valve 72 of this example of the invention is a three position solenoid operated valve which is spring biased to a center position at which the flow paths to both ends of the ram are closed and thus the ram is immobilized. A pilot solenoid 74a and control switch 76a enable shifting of valve 72 to a second position at which fluid is applied to the head end of ram 39 and drained from the rod end. This pivots receptacle 27 downwardly as previously described to dump the contents of the receptacle. Closing of another control switch 76b causes another pilot solenoid 74b to shift valve 72 to the third position at which fluid is transmitted to the rod end of ram 39 and drained from the head end. This causes the ram 39 to contract and thereby return receptacle 27 to its horizontally extending orientation.

Referring to FIGS. 4 and 5, above described components of the vacuum and steam system are situated in a first sub-housing 77 behind partition 59. Hydraulic circuit components are in another sub-housing 78. Manual controls, such as switches 64 and 70, are situated at a control panel 79 located at front wall 14 of housing 12.

The flexible vacuum hose 62 and steam hose 68 communicate with the interior of receptacle 27 through fittings 81 and 82 respectively which are at the underside of the receptacle, the hoses being of sufficient length to provide slack for enabling the pivoting movement of the receptacle. Referring to FIGS. 1 and 2, a manifold plate 83 having spaced apart apertures 84 extends across the bottom region of the receptacle 27. Plate 83 holds the wastes above any condensed steam or other liquid that may be present at the bottom of the receptacle, distributes incoming steam throughout the receptacle and prevents blockage of the vacuum and steam fittings 81 and 82 by wastes which are contained in the receptacle.

Referring again to FIGS. 4 and 5, the compact and mechanically uncomplicated construction of the waste processor 11 enables easy movement or reorientation of the installation if that should be desired. Repositioning of the waste processor 11 is facilitated if it is provided with ground wheels 86 of which one pair are preferably caster wheels.

In operation, the receptacle 27 with its closure door 47 provides a sealed fluid tight storage area for successive batches of infectious waste. Periodically the accumulated wastes are sterilized by activating vacuum pump 61 to withdraw air from the receptacle and then opening valve 67 to admit pressurized steam to the receptacle. Vacuum pump 61 may be operated at a reduced rate while steam is being admitted to the receptacle 27 to remove cooled and/or condensed steam. Steam exposure times of one half hour or more are typically required to effect complete sterilization.

At the end of the sterilization cycle, the inflow of steam is stopped by closing valve 67. The contents of receptacle 27 may be allowed to cool or vacuum pump 61 may be operated for a period to remove steam and reduce pressure in the receptacle. Closure door 47 is then opened and swung away from the open end 28 of the receptacle. Ram control valve 72 is operated to cause extension of ram 39. This pivots the open end 28 downward in the previously described manner and dumps the sterilized wastes into receiver cart 23. A subsequent contraction of ram 39 restores the receptacle to the waste receiving orientation. Receiver cart 23 is then withdrawn from the waste processor 11 and is either emptied into a garbage dumpster or the like and returned or, alternately, used as a temporary storage for sterilized waste in which case another similar receiver cart is entered into the waste processor.

Thus the invention provides for safe and efficient storage and sterilization of infectious wastes in an installation which is compact, mechanically simple and of an economical construction. While the invention has been described with respect to a single embodiment for purposes of example, many modifications and variations of the construction are possible and it is not intended to limit the invention except as defined in the following claims.

I claim:

1. Apparatus for sterilizing bio-hazardous waste materials comprising:

a housing having an upper region bounded in part by a front face of said housing which front face has an upper access opening for enabling entry of waste materials that are to be sterilized, said housing having a lower region and a lower access opening thereat constructed and arranged for enabling entry of a removable sterilized waste receiver into said lower region of said housing and withdrawal of said waste receiver therefrom;

an unsterilized waste receptacle disposed in said upper region of said housing and which has an open end and a closed end, said receptacle being pivotable about a horizontal pivot axis which extends in parallel relationship with said front face of said housing and in parallel relationship with said upper access opening, said receptacle being pivotable about said axis between a first orientation at which said open end is in register with said upper access opening of said housing and an upended orientation at which said open end is below said closed end and at least partially faces said lower region of said housing;

a closure disposed at said front face of said housing and being coupled thereto and means for enabling movement of said closure between an open position at which unsterilized waste materials may be inserted into said receptacle through said upper access opening when said receptacle is at said first orientation and a closed position at which said closure seats at said open end of said receptacle and closes said receptacle; and means for sterilizing waste materials while said waste materials are within said receptacle.

2. The apparatus of claim 1 wherein said housing has opposite side members which extend rearwardly from said front face of said housing and wherein said horizontal pivot axis is defined by first and second aligned pivot couplings connected between said unsterilized waste receptacle and said opposite side members of said housing.

3. The apparatus of claim 2 wherein said receptacle has a first wall region that is uppermost when said receptacle is at said first orientation and a second wall region that is lowermost when said receptacle is at said first orientation and wherein said first and second pivot couplings are situated substantially midway between said first and second wall regions.

4. The apparatus of claim 3 wherein said pivot couplings are situated substantially midway between said open and closed ends of said receptacle.

5. The apparatus of claim 1 further including an extendible and contractible fluid actuator having a first end coupled to one of said housing side members and an opposite end coupled to said receptacle at a location thereon that is spaced apart from said horizontal pivot axis.

6. The apparatus of claim 1 wherein said lower access opening is situated at said front face of said housing at a location which is below said upper access opening.

7. The apparatus of claim 1 wherein said housing has a stepped profile at said front face of said housing forming a shelf which extends outward from the plane of said first access opening and which causes said lower region of said housing to extend outward from said upper region thereof, said lower access opening being at the outward extending lower region of said front face of said housing.

8. The apparatus of claim 1 wherein portions of said housing form only the sides and the top of said lower access opening, the base of said lower access opening being defined by the surface on which said apparatus rests and wherein at least a portion of said lower region of said housing that is adjacent said lower access opening is open at the bottom whereby wheeled sterilized waste receivers may be rolled into and out of said lower region of said housing while remaining in contact with said surface.

9. The apparatus of claim 1 further including a removable sterilized waste receiver, said waste receiver being situated directly below said waste receptacle including when said receptacle is at said first orientation.

10. Apparatus for storing and sterilizing bio-hazardous wastes comprising:

a housing having a front wall, back wall and opposite side members which extend therebetween and having an upper access opening for enabling insertion of wastes which are to be sterilized and further having a lower access opening proportioned to enable insertion of a sterilized waste receiver into said housing and withdrawal of said receiver therefrom, a receptacle disposed within said housing and having an open end and a closed end, said receptacle being formed of fluid impervious material, pivot means for enabling pivoting of said receptacle between a first orientation at which said open end of said receptacle is substantially coincident with said upper access opening of said housing and a second orientation at which said open end faces at least partially in a downward direction within said housing and wherein said pivot means pivots said receptacle between said orientations about a horizontal axis of rotation that extends in parallel relationship with said front wall of said housing and in parallel relationship with said upper access opening, a receptacle closure situated at said front wall of said housing and a hinge coupling said closure to said housing and which enables movement of said closure between an open position at which said open end of said receptacle is exposed at said upper access opening and a closed position at which said closure seats at said open end of said receptacle and seals said receptacle, and means for sterilizing waste materials while said waste materials are within said receptacle and said receptacle is at said first orientation and is sealed by said closure.

11. The apparatus of claim 10 wherein said pivot means includes first and second pivot couplings connected between said receptacle and said side members of said housing at opposite sides of said receptacle, said pivot couplings being aligned along said axis of rotation and wherein said axis of rotation intersects said receptacle.

12. The apparatus of claim 11 wherein said axis of rotation is substantially midway between uppermost and lowermost portions of said receptacle and substantially midway between said open end and closed end thereof.

13. The apparatus of claim 10 wherein said housing has a lower region which extends forward from the plane of said front wall at the base of said front wall and which has a front end at which said lower access opening is located.

14. The apparatus of claim 12 further including a wheeled waste receiver cart disposed within said housing directly below said waste receptacle and having proportions which enable withdrawal of said cart through said lower access opening.

\* \* \* \* \*